United States Patent
Pradhan et al.

(10) Patent No.: US 11,331,485 B2
(45) Date of Patent: May 17, 2022

(54) SYSTEM AND METHOD FOR INTEGRATING THREE DIMENSIONAL VIDEO AND GALVANIC VESTIBULAR STIMULATION

(71) Applicant: Mayo Foundation for Medical Education and Research, Rochester, MN (US)

(72) Inventors: Gaurav N. Pradhan, Fountain Hills, AZ (US); Michael J. Cevette, Cave Creek, AZ (US); Jan Stepanek, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 54 days.

(21) Appl. No.: 15/778,941

(22) PCT Filed: Dec. 19, 2016

(86) PCT No.: PCT/US2016/067560
§ 371 (c)(1),
(2) Date: May 24, 2018

(87) PCT Pub. No.: WO2017/112593
PCT Pub. Date: Jun. 29, 2017

(65) Prior Publication Data
US 2018/0343433 A1    Nov. 29, 2018

Related U.S. Application Data

(60) Provisional application No. 62/387,586, filed on Dec. 23, 2015.

(51) Int. Cl.
*A61N 1/36* (2006.01)
*G06F 3/01* (2006.01)
*A61N 1/04* (2006.01)

(52) U.S. Cl.
CPC .......... *A61N 1/36036* (2017.08); *G06F 3/011* (2013.01); *G06F 3/012* (2013.01); *A61N 1/0456* (2013.01); *A61N 1/36031* (2017.08)

(58) Field of Classification Search
CPC .... H04N 13/111; H04N 13/366; H04N 5/222; A61N 1/36036; A61N 1/0456; A61N 1/36014; G06F 3/011; G06F 3/012
(Continued)

(56) References Cited

U.S. PATENT DOCUMENTS

| 906,330 A | 12/1908 | Stonemetz |
| 5,351,966 A * | 10/1994 | Tohyama ................ A63F 13/52 463/2 |

(Continued)

FOREIGN PATENT DOCUMENTS

JP    2011523515 A    8/2011

OTHER PUBLICATIONS

Extended European Search Report issued in EP Application No. 16879936.9, dated Jun. 19, 2019, 13 pages.
(Continued)

*Primary Examiner* — Loi H Tran

(57) ABSTRACT

A method for providing galvanic vestibular stimulation corresponding to accelerations in scenes of a video. Embodiments include (1) receiving a three dimensional video signal including three dimensional video angular velocity information, (2) receiving a three dimensional head orientation signal including three dimensional head angular velocity information, (3) calculating resultant three dimensional angular velocity information based on the video angular velocity information and the head angular velocity information, (4) calculating three dimensional acceleration information based on the resultant three dimensional angular velocity information, and (5) generating three dimensional
(Continued)

galvanic vestibular stimulation signals corresponding to the resultant three dimensional angular acceleration information, wherein the three dimensional stimulation signals will stimulate three dimensional acceleration sensations corresponding to accelerations on the user viewing the displayed scenes.

8 Claims, 1 Drawing Sheet

(58) Field of Classification Search
USPC .......................................................... 348/46
See application file for complete search history.

(56) References Cited

U.S. PATENT DOCUMENTS

| | | | |
|---|---|---|---|
| 5,762,612 | A | 6/1998 | Campbell |
| 5,963,664 | A * | 10/1999 | Kumar ..................... G06K 9/32 |
| | | | 382/154 |
| 8,718,796 | B2 | 5/2014 | Cevette et al. |
| 2003/0073922 | A1 | 4/2003 | Miller et al. |
| 2004/0027353 | A1 * | 2/2004 | Saito ....................... G06T 13/00 |
| | | | 345/473 |
| 2010/0113150 | A1 | 5/2010 | Chan et al. |
| 2011/0029045 | A1 | 2/2011 | Cevette et al. |
| 2011/0044604 | A1 | 2/2011 | Brokken et al. |
| 2011/0267442 | A1 * | 11/2011 | Imai ..................... H04N 13/354 |
| | | | 348/56 |
| 2012/0105602 | A1 * | 5/2012 | McNamer ................ G06T 7/20 |
| | | | 348/50 |
| 2012/0154396 | A1 * | 6/2012 | Atkins ................... G02B 30/26 |
| | | | 345/419 |
| 2013/0171596 | A1 | 7/2013 | French |
| 2016/0045733 | A1 * | 2/2016 | McGeoch ............ A61N 1/0526 |
| | | | 607/60 |

OTHER PUBLICATIONS

Fitzpatrick, R. C. and Day, B. L. (2004). Probing the human vestibular system with galvanic stimulation. J. Appl. Physiol., 96:2301-2316, 2004, 16 pages.

International Preliminary Report on Patentability issued in PCT/US2016/067560, 9 pages, dated Jul. 5, 2018.

International Search Report and Written Opinion issued in PCT/US2016/067560, dated Mar. 31, 2017, 12 pages.

* cited by examiner

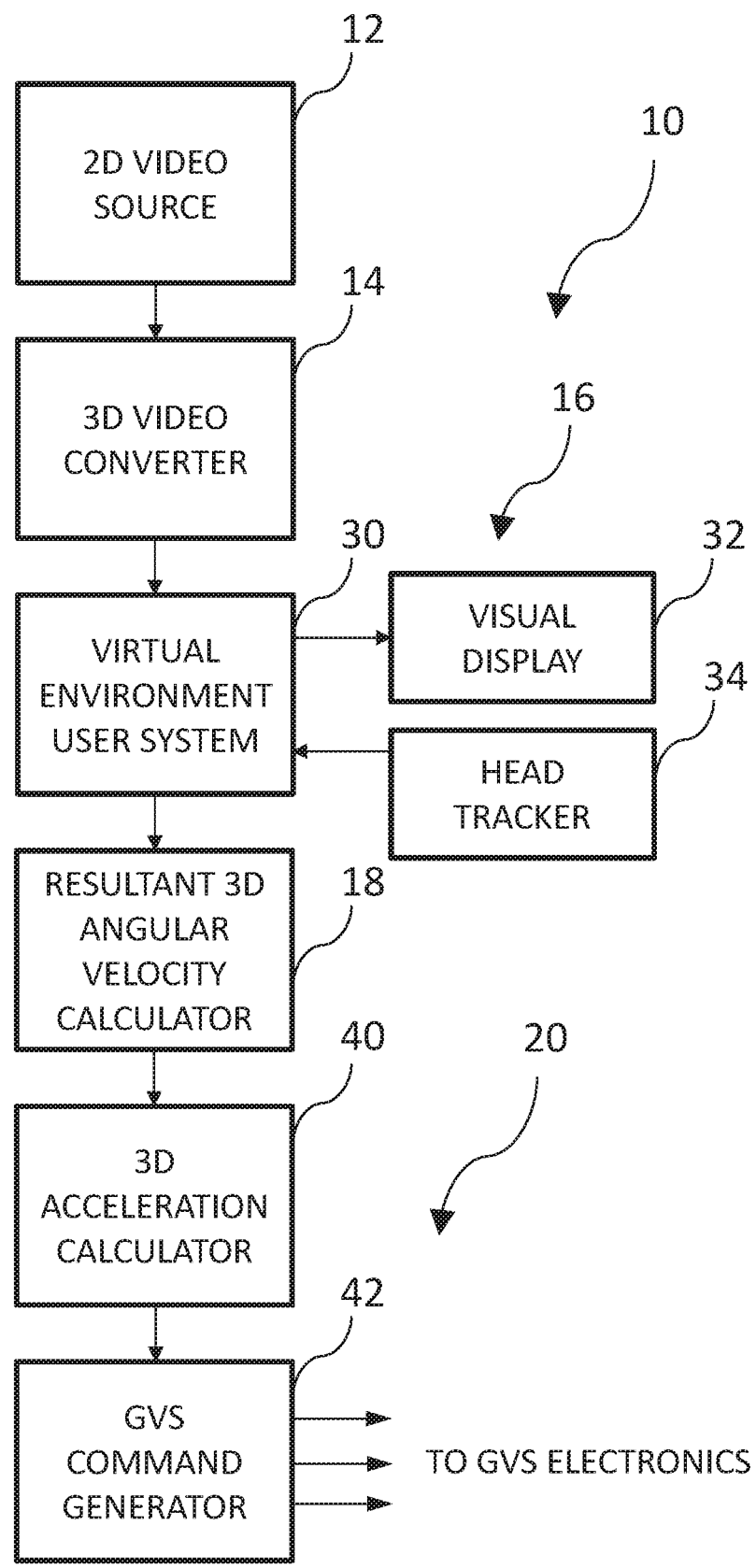

SYSTEM AND METHOD FOR INTEGRATING THREE DIMENSIONAL VIDEO AND GALVANIC VESTIBULAR STIMULATION

CROSS REFERENCE TO RELATED APPLICATION

This application is a national phase application of PCT Application No. PCT/US2016/067560, internationally filed on Dec. 19, 2016, which claims the benefit of U.S. Provisional Application No. 62/387,586, filed Dec. 23, 2015, both of which are herein incorporated by reference in their entireties.

FIELD OF THE INVENTION

The invention relates generally to virtual reality stimulation systems. In particular, the invention relates to the integration of galvanic vestibular stimulation with three dimensional video.

BACKGROUND

So-called virtual reality or enhanced reality systems such as the Rift device developed by Oculus VR present three dimensional visual stimulation to a user by displaying three dimensional video on a headset. Information representative of the orientation and/or movement of the user's head is tracked by a tracking device, and that information is used by the system to control the display of the video (e.g., so the scenes in the displayed video properly correspond to those in the direction that the user turns his or her head). It is also known to provide galvanic vestibular stimulation (GVS) in conjunction with the visual stimulation in order to provide the user with a sense of motion or acceleration to enhance the virtual experience. Systems of these types are disclosed, for example, in the Campbell U.S. Pat. No. 5,762,612, LaValle et al. U.S. Pat. No. 9,063,30, and the Brokken et al. U.S. Patent Application Publication 2011/0044604, all of which are incorporated herein by reference in their entireties and for all purposes. GVS systems are disclosed, for example, in the Cevette et al. U.S. Pat. No. 8,718,796, which is incorporated herein by reference in its entirety and for all purposes. There remains, however, a continuing need for enhanced virtual reality systems. In particular, there is need for such systems that provide enhanced integrated vestibular stimulation corresponding to the visual stimulation.

SUMMARY

Embodiments of the invention include a method for providing galvanic vestibular stimulation corresponding to accelerations in scenes of a video. In embodiments, the method comprises (1) receiving a three dimensional video signal including three dimensional video angular velocity information, wherein the video signal is representative of scenes that can be displayed to a user; (2) receiving a three dimensional head orientation signal including three dimensional head angular velocity information, wherein the head orientation signal is representative of the of the orientation of the head of the user viewing the displayed scenes; (3) calculating resultant three dimensional angular velocity information based on the video angular velocity information and the head angular velocity information, wherein the resultant three dimensional angular velocity information is representative of three dimensional angular velocities of the user with respect to the viewed scenes; (4) calculating three dimensional acceleration information based on the resultant three dimensional angular velocity information, wherein the three dimensional acceleration information is representative of three dimensional accelerations of the user viewing the scenes; and (5) generating three dimensional galvanic vestibular stimulation signals corresponding to the resultant three dimensional angular acceleration information, wherein the three dimensional stimulation signals will stimulate three dimensional acceleration sensations corresponding to accelerations on the user viewing the displayed scenes. The three dimensions represent velocities or accelerations about at least three axes, such as pitch, yaw and roll, in embodiments. Embodiments also include (1) receiving a two dimensional video signal; and (2) generating the three dimensional video signal based on the two dimensional video signal.

DESCRIPTION OF THE DRAWINGS

FIG. 1 is a block diagram of a three dimensional video and galvanic vestibular stimulation system in accordance with embodiments of the invention.

DESCRIPTION OF THE INVENTION

A system 10 and method to provide integrated three dimensional (3D) video and corresponding 3D galvanic vestibular stimulation (GVS) in accordance with embodiments of the invention can be described with reference to FIG. 1. As shown, the system 10 includes two dimensional (2D) video source 12, 3D video converter 14, 3D visual stimulation system 16, resultant 3D angular velocity calculator 18 and GVS stimulation system 20. 2D video source 12 can be any desired source of a 2D video data or signal. Examples of video source 12 include a TV receiver, a DVD or other playback device, video game console, drone camera or other camera that provides 2D video signals representative of video visual scenes such as TV programming, movies, video game fields and scenes captured by a camera. In embodiments, the output of the 2D video source 12 is a composite video signal. The 2D video signal provided by the video source 12 is coupled to the 3D video converter 14. 3D video converter 14 is configured to receive a video signal over a Universal Serial Bus (USB) in embodiments of the invention. In such embodiments configured for use with a 2D video source 12 that outputs a composite video signal, a composite-to-USB converter (not shown) can be coupled between the 2D video source and the 3D video converter 14. 2D video source 12 can provide video in other formats and 3D video converter 14 can receive video in other formats in other embodiments of the invention.

3D video converter 14 converts the received 2D video signal into a corresponding 3D video data or signal. In embodiments, the 3D video converter 14 includes a computer executing Open GL (Open Graphics Library). Other embodiments are based on other 3D video formats. The 3D video signal generated by video converter 14 includes data representative of 3D video angular velocity information characteristic of the motion in the corresponding scenes of the 3D video. For example, the 3D video angular velocity information can be numerically expressed as angular velocities in each of the pitch, yaw and roll directions and represented in matrix form. In embodiments, the 3D video signal produced by the video converter 14 has a format compatible with the 3D visual stimulation system 16. Other embodiments (not shown) include a converter for converting the 3D video signal produced by the video converter 14 to a format compatible with the stimulation system 16.

3D visual stimulation system 16 includes a virtual environment user system 30, visual display 32 and head tracker 34 in the illustrated embodiment. Visual display 32 is driven by the virtual environment user system 30 and provides a 3D visual display of the 3D video received from the 3D video converter 14. In embodiments, the visual display 32 is an Oculus Rift head-mounted display of the type developed by Oculus VR. Other virtual reality display systems are used in other embodiments. Head tracker 34 generates, and provides to the virtual environment user system 30, information or signals representative of the orientation of the user's head or eyes while the user is viewing the video on the visual display 32. Head tracker 34 can, for example, be built into the visual display 32 (e.g., including accelerometers that detect motion), and/or can be external devices such as sensors. The head orientation information provided by head tracker 34 can be in the form of 3D head angular velocities representative of the user's head motion. In embodiments, the head angular velocity information provided by head tracker 34 is numerically expressed as angular velocities in each of the pitch, yaw and roll directions of the head, and is represented in matrix form. Virtual environment user system 30, which can, for example, be a video game console or a general purpose computer with video driver hardware and software, drives the visual display 32 in response to the received video signal from 3D video converter 14 and the head orientation information provided by head tracker 34 to provide the user with a visual virtual reality environment corresponding to the video and the movement of his or her head.

Resultant angular velocity calculator 18 receives the 3D video angular velocity information and the 3D head angular velocity information. In the illustrated embodiment, this video and head angular velocity information is received through the virtual environment user system 30. In other embodiments (not shown), either or both of the 3D video and head angular velocity information can be received directly from the 3D video converter 14 or the head tracker 34, respectively. Angular velocity calculator 18 calculates resultant 3D angular velocities on the basis of both the video and head motion angular velocities (i.e., the corresponding angular velocities of the user with respect to the viewed scenes of the video), and provides signals representative of that information. In embodiments, the resultant 3D angular velocities are expressed as angular velocities in each of the pitch, yaw and roll directions, and are represented in matrix form. Angular velocity calculator 18 is a programmed computer in embodiments. GVS stimulation system 20 is coupled to receive the resultant 3D angular velocity information from the angular velocity calculator 18, and generates 3D GVS commands or signals that can be applied to the user through electrodes (not shown). The 3D GVS signals stimulate 3D acceleration sensations that correspond to the accelerations on the user viewing the video scenes. The illustrated embodiment of GVS stimulation system 20 includes 3D acceleration calculator 40 and GVS command generator 42. 3D acceleration calculator 40 processes the resultant 3D angular velocity information and calculates 3D acceleration information associated with the angular velocity information (e.g., determines the changes in the 3D angular velocities). In embodiments, the 3D acceleration information represents accelerations in each of the pitch, yaw and roll directions. 3D acceleration calculator 40 is a programmed computer in embodiments.

GVS command generator 42 converts the 3D acceleration information into electrical signals suitable and appropriate for application to the user's body (e.g., through electrodes) that will stimulate the corresponding 3D acceleration sensations in the user. In embodiments, command generator 42 generates GVS signals that provide stimulation representative of acceleration in each of the pitch, yaw and roll dimensions. In embodiments, GVS stimulation system 20 can be a four channel system that provides motion perception through four electrodes placed on the left mastoid, forehead, right mastoid, and the nape of the neck. The amplitude, locations and/or timing of the commands applied to the various electrodes can be controlled to provide GVS commands in real time in response to the 3D angular velocity information provided by angular velocity calculator 18, thereby stimulating motion perceptions corresponding to the visual stimulation presented to the user. By way of example, approaches such as those disclosed in the above-identified Cevette et al. U.S. Pat. No. 8,718,796 can be used for this purpose. Other embodiments include other electrode numbers and placement configurations, and other stimulation approaches In embodiments, 3D video converter 14, virtual environment user system 30, resultant 3D angular velocity calculator 18 and 3D acceleration calculator 40 can be implemented by separate computer systems or processors. In other embodiments, 3D video converter 14, virtual environment user system 30, resultant 3D angular velocity calculator 18 and 3D acceleration calculator 40 represent logical functions, and all or some or all of these functions can be performed by other computer system architectures. For example, the functions performed by 3D video converter 14, virtual environment user system 30 and resultant angular velocity calculator 18 can be provided by a GVS motion app on one computer system.

Embodiments of the invention offer important advantages. For example, they can enhance the virtual reality experience of users by providing motion stimulation that closely represents the motion corresponding to the video scene. The system and method are flexible in that they can be used in connection with any desired 2D video source. The system and method are also efficient to implement.

Although the invention has been described with reference to preferred embodiments, those skilled in the art will recognize that changes can be made in form and detail without departing from the spirit and scope of the invention. For example, as used herein, the term "virtual reality" is intended to broadly encompass any system and method that provides at least in part electronically generated stimulation to a user, including for example so-called "augmented reality" environments.

The following is claimed:

1. A method for providing galvanic vestibular stimulation to a user corresponding to scenes of a video being viewed by the user using a virtual reality visual display in a virtual environment user system where the user's body, with the exception of the user's head or eyes, is substantially stationary with respect to the visual display, comprising:

receiving a three dimensional video signal, wherein the video signal is representative of scenes of the video being viewed by the user, and includes data representative of three dimensional video angular velocity information of motion in the corresponding scenes of the video;

receiving a three dimensional head orientation signal including three dimensional head angular velocity information, wherein the head orientation signal is representative of the motion of the head or eyes of the user viewing the scenes on the virtual reality visual display in the virtual environment user system where the user's body, with the exception of the user's head or eyes, is substantially stationary with respect to the visual display;

calculating resultant three dimensional angular velocity information based on the video angular velocity information and the head angular velocity information, wherein the resultant three dimensional angular velocity information is representative of three dimensional angular velocities of the user's head or eyes with respect to the motion in the viewed scenes;

calculating three dimensional acceleration information based on the resultant three dimensional angular velocity information, wherein the three dimensional acceleration information is associated with the resultant three dimensional angular velocity information and is representative of three dimensional accelerations of the user's head or eyes while the user is viewing the scenes on the virtual reality visual display in the virtual environment user system where the user's body, with the exception of the user's head or eyes, is substantially stationary with respect to the visual display; and generating three dimensional galvanic vestibular stimulation signals corresponding to the three dimensional acceleration information, wherein the three dimensional stimulation signals are configured to stimulate three dimensional acceleration sensations corresponding to accelerations of the head or eyes while the user is viewing the scenes on the virtual reality visual display in the virtual environment user system where the user's body, with the exception of the user's head or eyes, is substantially stationary with respect to the visual display.

2. The method of claim 1 wherein the three dimensional video signal and the three dimensional head orientation signal are characteristic of motion in at least three directions.

3. The method of claim 2 wherein the at least three directions include pitch, yaw and roll directions.

4. The method of claim 3 and further including:
receiving a two dimensional video signal; and
generating the three dimensional video signal based on the two dimensional video signal.

5. The method of claim 2 and further including:
receiving a two dimensional video signal; and
generating the three dimensional video signal based on the two dimensional video signal.

6. The method of claim 1 and further including:
receiving a two dimensional video signal; and
generating the three dimensional video signal based on the two dimensional video signal.

7. The method of claim 6 and further including:
displaying the scenes represented by the video to the user; and
applying the three dimensional stimulation signals to the user while displaying the scenes.

8. The method of claim 1 and further including:
displaying the scenes represented by the video to the user; and
applying the three dimensional stimulation signals to the user while displaying the scenes.

* * * * *